United States Patent
Banin et al.

(10) Patent No.: US 11,667,601 B2
(45) Date of Patent: Jun. 6, 2023

(54) CALCIUM BOPTA COMPLEX

(71) Applicant: BRACCO IMAGING S.P.A., Milan (IT)

(72) Inventors: Andrea Banin, Collegno (IT); Laura Galimberti, Fara Gera d'adda (IT); Roberta Napolitano, Albiano d'Ivrea (IT); Roberta Fretta, Collegno (IT)

(73) Assignee: BRACCO IMAGING S.P.A., Milan (IT)

( * ) Notice: Subject to any disclaimer, the term of this patent is extended or adjusted under 35 U.S.C. 154(b) by 0 days.

(21) Appl. No.: 17/786,623

(22) PCT Filed: Dec. 17, 2020

(86) PCT No.: PCT/EP2020/086699
§ 371 (c)(1),
(2) Date: Jun. 17, 2022

(87) PCT Pub. No.: WO2021/122941
PCT Pub. Date: Jun. 24, 2021

(65) Prior Publication Data
US 2023/0046541 A1  Feb. 16, 2023

(30) Foreign Application Priority Data
Dec. 20, 2019 (EP) .................................. 19218669

(51) Int. Cl.
*C07C 229/22* (2006.01)
*C07C 227/18* (2006.01)

(52) U.S. Cl.
CPC .......... *C07C 229/22* (2013.01); *C07C 227/18* (2013.01)

(58) Field of Classification Search
CPC ........................... C07C 229/22; C07C 227/18
See application file for complete search history.

(56) References Cited

U.S. PATENT DOCUMENTS

| 5,876,695 A | 3/1999 | Gries et al. |
| 9,447,053 B2 | 9/2016 | Platzek et al. |

FOREIGN PATENT DOCUMENTS

| EP | 1210353 B1 | 7/2003 |
| WO | 2016012386 A1 | 1/2016 |

OTHER PUBLICATIONS

International Search Report and Written Opinion for PCT/EP2020/086699, dated Mar. 16, 2021.
Uggeri, F., et al., "Novel Contrast Agents for Magnetic Resonance Imaging. Synthesis and Characterization of the Ligand BOPTA and Its Ln(III) Complexes (Ln=Gd, La, Lu). X-ray Structure of Disodium (TPS-9-145337286-C-S)-[4-Carboxy-5,8,11-tris(carboxymethyl)-1-phenyl-2-oxa-5,8,11-triazatridecan-13-oato(5-)]gadolinate(2-) in a Mixture with Its Enantiomer," Inorg. Chemistry, 34:633-642 (1995).
Wax, P. M., "Current Use of Chelation in American Health Care," J. Med. Toxicol. 9:303-307 (2013).

*Primary Examiner* — Jeffrey S Lundgren
*Assistant Examiner* — William Y Lee
(74) *Attorney, Agent, or Firm* — Vivicar Law, PLLC

(57) ABSTRACT

The present invention relates to the calcium complex of (4RS)(4-carboxy-5,8,11-tris(carboxymethyl)-1-phenyl oxa-5,8,11-triazatridecan-13-oato(5-))pentahydrogen (BOPTA) in the form of a salt, to the process for its preparation and to a formulation comprising said salt.

19 Claims, No Drawings

CALCIUM BOPTA COMPLEX

CROSS-REFERENCE TO RELATED APPLICATIONS

This application is the national stage application of corresponding international application number PCT/EP2020/086699, filed Dec. 17, 2020, which claims priority to and the benefit of European application no. 19218669.0, filed Dec. 20, 2019, which is hereby incorporated by reference in its entirety.

FIELD OF INVENTION

The present invention generally relates to the calcium complex of (4RS)(4-carboxy-5,8,11-tris(carboxymethyl)-1-phenyl-2-oxa-5,8,11-triazatridecan-13-oato(5-)) pentahydrogen (BOPTA) in the form of a salt, its preparation and its use in the preparation of pharmaceutical compositions comprising it.

BACKGROUND OF THE INVENTION

Metal chelated complexes, more commonly with Calcium ($Ca^{2+}$) and Zinc ($Zn^{2+}$), are known in medicine for the treatment of heavy metals, including metal ions and radioactive nuclides. For instance, Ref. 1 (Wax, P. M., *J. Med. Toxicol.* 2013, 9:303-307) reports the currently FDA-approved chelators on the market, proposed as scavenging agents.

Examples of Calcium complexes are described in Ref. 2 (U.S. Pat. No. 9,447,053 (B2)—Bayer Intellectual Property GmbH), and Ref. 3 (EP1210353) or Ref. 4 (U.S. Pat. No. 5,876,695—Schering AG).

Applicant has now found a new Calcium complex compound, namely the Calcium complex compound of the (4RS)-[4-carboxy-5,8,11-tris(carboxymethyl)-1-phenyl-2-oxa-5,8,11-triazatridecan-13-oato(5-)]pentahydrogen chelating ligand, otherwise known as BOPTA. Applicant has also found a new synthetic procedure allowing an advantageous preparation and isolation of such compound.

As a matter of fact, the Applicant observed that the known manufacturing methods (see for instance Ref. 5 (WO2016012386)) for preparing a solid form of the gadobenate (Gd-BOPTA) dimeglumine cannot be used for an effective preparation of Ca-BOPTA.

The Applicant has now unexpectedly found that a calcium complex of BOPTA can be obtained in a solid and conveniently filterable physical form, as a salt, using appropriate operative conditions.

Therefore, for the first time the Applicant proposes a process for the manufacturing of Ca-BOPTA salt in a solid form, suitable for a pharmaceutical use. The proposed process allows to obtain a solid product that can advantageously be used for the manufacturing of a pharmaceutical solution, due to its good solubility, good flowability, good yield and high quality.

SUMMARY OF THE INVENTION

The present invention generally relates to the calcium complex of (4RS)(4-carboxy-5,8,11-tris(carboxymethyl)-1-phenyl-2-oxa-5,8,11-triazatridecan-13-oato(5-))pentahydrogen (BO PTA) and salts thereof, their preparation and their use in the preparation of pharmaceutical compositions comprising them.

In a preferred aspect, the invention relates to the calcium complex of BOPTA as salt of formula (I):

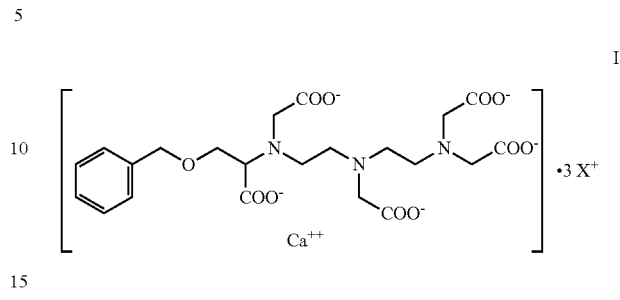

Where $X^+$ represents a monovalent cation, preferably selected from an alkali metal, including sodium ($Na^+$) or potassium ($K^+$), and ammonium ($NH_4^+$), more preferably $Na^+$.

Another aspect of the invention relates to a process for the preparation of a solid form of the compound of formula I.

In a further aspect, the invention relates to a pharmaceutical composition comprising the compound of formula I in admixture with one or more physiologically acceptable carriers, diluents and galenic excipients.

DETAILED DESCRIPTION OF THE INVENTION

In the present description and claims, the term BOPTA indicates the chelating agent (4RS)-[4-carboxy-5,8,11-tris(carboxymethyl)-1-phenyl-2-oxa-5,8,11-triazatridecan-13-oato(5-)]pentahydrogen of formula (III):

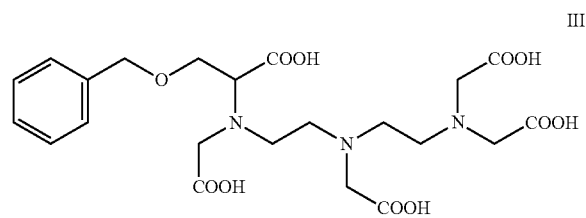 [SMILES: O=C(O)CN(CCN(CC(=O)O)CC(=O)O)CCN(CC(=O)O)C(COCc1ccccc1)C(=O)O]

or its anionic form of formula (III'):

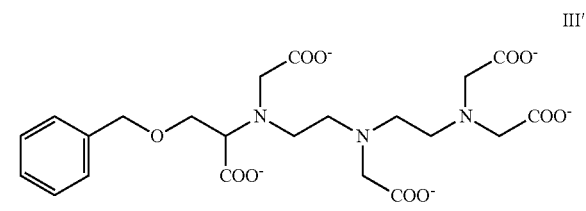

or any partial anionic form thereof.

In this description and claims, the expressions chelating agent and ligand, are used interchangeably.

As defined herein the calcium complex of BOPTA (in anionic form) is a compound of formula (II):

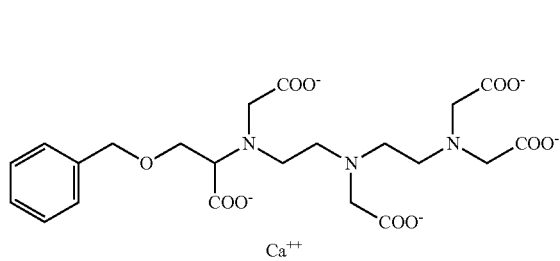

The term "complex" has its conventional meaning in the chemistry field. It generally indicates any metal complex comprising a central metal atom or ion that is coordinated to one or more ligands, which are ions or molecules that contain one or more pairs of electrons that can be shared with the metal.

The complex of formula II of the present invention comprises calcium ion (i.e. $Ca^{2+}$) as coordination centre and BOPTA as chelating agent. Preferred according to the invention are BOPTA mono-calcium complex compounds, having a single calcium complexed to the BOPTA ligand. The BOPTA ligand can be in full or partial ionic form.

In the present description and claims, the calcium complex of BOPTA of formula II is indicated interchangeably as Ca-BOPTA, or Ca-BOPTA complex or calcium complex of BOPTA.

An aspect of the present invention relates to Ca-BOPTA complex of formula II in the form of a pharmaceutically acceptable salt. The term "pharmaceutically acceptable salt" as used herein refers to Ca-BOPTA complex wherein at least one of the carboxylic groups of BOPTA, not involved into the complexation of the calcium ions, is present in ionic form (i.e. $-COO^-$) and interacts with a corresponding cation of a physiologically compatible base. The actual number of said free carboxylic acid groups may depend for instance on the pH of the solution containing the complex.

Examples of suitable cations which can be used to prepare a salt of Ca-BOPTA are inorganic (monovalent) cations. Preferred cations comprise the group of alkali ions, such as potassium ($K^+$) and sodium ($Na^+$), or the ammonium ion ($NH_4^+$).

In a preferred embodiment, this invention relates to the calcium complex of BOPTA as trisodium salt of formula Ia:

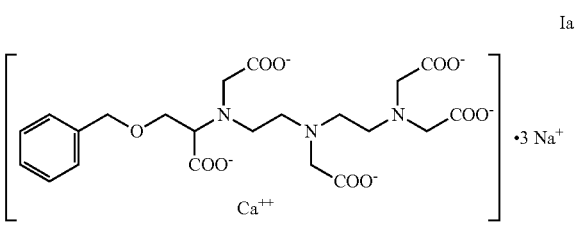

The compound of formula Ia can also be indicated as (4RS)-[4-carboxy-5,8,11-tris(carboxymethyl)-1-phenyl-2-oxa-5,8,11-triazatridecan-13-oato(5-)] calciate(3-) trisodium.

The expressions "calcium complex trisodium salt of formula Ia" and "compound of formula Ia" are used interchangeably in this description and claims.

Another aspect of the invention relates to a process for the preparation of a solid form of the compound of formula I, that comprises:

a) obtaining an aqueous solution of the compound of formula I by admixing a compound comprising calcium ion, the ligand BOPTA and a compound comprising the cation X in an aqueous solvent;
b) optionally adjusting the pH of the solution obtained at step a);
c) adding ethanol to the obtained solution, to achieve the precipitation of a solid form of compound of formula I;
d) collecting the obtained solid form of the calcium complex of formula I.

The process of the present invention allows the isolation of a crystalline solid form the compound of formula I that advantageously complies with the quality standards fixed by international authorities for pharmaceutical compounds.

Step a)

The step a) of the process of this invention comprises obtaining an aqueous solution of the compound of formula I by admixing a compound comprising calcium ion, the ligand BOPTA and a compound comprising the cation X in an aqueous solvent.

Said aqueous solvent is preferably selected from the group of highly polar solvents including water, saline solutions and highly polar organic solvent, and suitable mixtures thereof. More preferably said aqueous solvent comprises water.

The expression "compound comprising calcium ion ($Ca^{2+}$)", in short "Calcium compound", as used herein refers to electrically neutral compounds (without a net charge) consisting of an ionic assembly of calcium cations and anions. Suitable calcium compounds include calcium hydroxide ($Ca(OH)_2$), calcium carbonate ($CaCO_3$), calcium acetate ($Ca(CH_3COO)_2$), calcium oxide ($CaO_2$) and calcium chloride ($CaCl_2$)). According to this invention, the compound comprising calcium ion is preferably calcium hydroxide or calcium carbonate.

In an embodiment of the invention, the compound comprising the cation X of step a) is a base, preferably an inorganic base, wherein the cation of said base is able to form a salt with the free carboxylic acid groups of BOPTA.

Examples of suitable inorganic bases comprise, for instance, hydroxides or carbonates of alkali metals, such as potassium carbonate ($K_2CO_3$), potassium bicarbonate ($KHCO_3$), potassium hydroxide (KOH), sodium carbonate ($Na_2CO_3$), sodium bicarbonate ($NaHCO_3$), sodium hydroxide (NaOH), and of ammonium, such as ammonium carbonate (($NH_4)_2CO_3$), ammonium bicarbonate (($NH_4)HCO_3$) and ammonium hydroxide ($NH_4OH$). Preferably the base of step a) is sodium hydroxide (i.e. NaOH).

As observed by the Applicant, unsatisfactory results (e.g. final products in the form of sticky solids with lumps) were obtained when adding an organic base or an alkaline earth metal base at the step a), to obtain for instance Ca-BOPTA complex as salt of meglumine or calcium.

In an embodiment of the invention, at step a) the compound comprising the cation X is admixed with a compound comprising calcium ion and the ligand BOPTA as an aqueous solution.

In an alternative embodiment, at step a) the compound comprising the cation X is admixed with a compound comprising calcium ion and the ligand BOPTA as a solid form.

In a preferred embodiment of the invention, at step a) the molar ratio between BOPTA and the compound comprising the cation X is preferably comprised between 1:1.5 and 1:3 mol/mol, more preferably from 1:2.5 to 1:3 mol/mol, still more preferably is 1:2.5 mol/mol.

Step a) leads to obtain an aqueous solution of the compound of formula I by admixing a compound comprising calcium ion, the ligand BOPTA and a compound comprising the cation X in an aqueous solvent and stirring the obtained admixture for 0.5 to 24 hours, preferably from 2 to 20 hours, more preferably for 4 hours.

According to this invention, during step a) a complexation reaction occurs between $Ca^{2+}$ ions and BOPTA. The product of this complexation reaction is the Ca-BOPTA complex of formula II.

At step a) the theoretical stoichiometric ratio between $Ca^{2+}$ ions and BOPTA is comprised from 2 to 0.5, preferably from 0.95 to 1.05, still more preferably is 1.

In an alternative embodiment, at the end of step a) an additional amount of the compound comprising calcium ion or of BOPTA can be admixed. Said additional amount allows to obtain an aqueous solution of the compound of formula I comprising no free ligand or free $Ca^{2+}$ or, alternatively, comprising a small excess of free $Ca^{2+}$ or free BOPTA.

In a preferred embodiment, at the end of step a), the aqueous solution of the compound of formula I contains an excess of free $Ca^{2+}$, wherein said excess is lower than 0.09 molar equivalents versus Ca-BOPTA (i.e. 9% mol/mol), more preferably lower than 0.05 molar equivalents (i.e. 5% mol/mol), down to $0.9 \times 10^{-4}$ molar equivalents (0.009% mol/mol).

As observed by the Applicant preparing the Ca-BOPTA trisodium salt using an excess of $Ca^{2+}$ higher than 10% mol/mol, may lead to obtain a final product less suitable for the pharmaceutical use. Unexpectedly, using an excess of calcium ions of about 2% mol/mol, at the end of the proposed process a suitable solid form of Ca-BOPTA trisodium was obtained, having good properties and good yield i.e. 94.5%.

Step b)

The optional step b) of the process of the invention comprises adjusting the pH of the aqueous solution of the compound of formula I obtained at step a), preferably by the addition of a base.

Step b) is necessary when the pH of the solution of step a) is not in the desired range.

In a preferred embodiment of the invention, at step b) the pH is adjusted to be comprised between 6.5 and 9.5, more preferably between 7.0 and 8.5 and, even more preferably close to 7.5.

As observed by the Applicant, aqueous solutions of the compound of formula I (in particular of formula Ia) having lower pH values, e.g. 6.1, led to the formation of a sticky lump final product. Similarly, pH values higher than 9.5, brought to a final product in the form of solid in blocks. In both these cases, at the end of the proposed process final products less suitable for the pharmaceutical use were obtained.

In an embodiment of the invention, the pH at step b) is adjusted by the addition of a base, preferably an inorganic base, wherein the cation of said base is able to form a salt with the free carboxylic acid groups of BOPTA.

According to this invention, examples of suitable inorganic bases at step b) comprise, for instance, hydroxides or carbonates of alkali metals, such as potassium carbonate ($K_2CO_3$), potassium bicarbonate ($KHCO_3$), potassium hydroxide (KOH), sodium carbonate ($Na_2CO_3$), sodium bicarbonate ($NaHCO_3$), sodium hydroxide (NaOH) and of ammonium, such as ammonium carbonate (($NH_4$)$_2CO_3$), ammonium bicarbonate (($NH_4$)$HCO_3$) and ammonium hydroxide ($NH_4OH$).

In a preferred embodiment of the invention, the base of step b) is the same base of step a). In a still more preferred embodiment, the base of step b) is sodium hydroxide.

In an alternative embodiment of the invention, the base of step b) comprises a cation different from the cation of the base of step a). In this alternative embodiment, a solution of Ca-BOPTA complex of formula II in the form of a mixed salt is obtained at the end of step b).

In this description, the expression "mixed salt" indicates a pharmaceutically acceptable salt of the Ca-BOPTA complex of formula II, wherein the carboxylic group of BOPTA, present in ionic form (i.e. $COO^-$) and not counterbalanced by the positive charge of the calcium ion, may interact with at least two different corresponding cations of physiologically compatible bases. The actual number of said free carboxylic acid groups may depend for instance on the pH of the solution containing the complex as, depending on the pH value, they may be in their respective protonated form.

In an embodiment of this invention, step a) and step b) of the proposed process are carried out at a reaction temperature comprised from 0° C. to 100° C., preferably from 10° C. to 80° C., still more preferably from 15° C. to 60° C.

In a preferred embodiment of this invention, at the end of the step b) a solution of the compound of formula I is obtained, wherein the concentration of said compound is comprised between 30% and 80% (w/w with respect to the total weight of solution), preferably between 40% and 75%, still more preferably between 45% and 70%.

Preferably, at the end of the step b) said aqueous solution of the compound of formula I is distilled to concentrate the solution and to obtain a solution of the compound of formula I having a concentration as above defined.

Said distillation process is preferably performed at a temperature comprised between 50° C. and 100° C., more preferably between 50° C. a 70° C., still more preferably between 50° C. and 60° C.

Said distillation process is preferably performed at atmospheric pressure (i.e. 101325 Pa) or, more preferably, at reduced pressure, e.g. comprised between 0 and $2.0 \times 10^4$ Pa, preferably between $2.5 \times 10^3$ and $1.5 \times 10^4$ Pa, more preferably between $5.0 \times 10^3$ and $1.0 \times 10^4$ Pa.

In an embodiment of the invention, said distillation process is performed at a temperature comprised between 50 and 60° C. and at a reduced pressure comprised between $5.0 \times 10^3$ and $1.0 \times 10^4$ Pa.

Step c)

According to the present invention, the step c) of the proposed process comprises adding ethanol to the obtained solution of Ca-BOPTA salt to achieve the precipitation of a solid form of the compound of formula I, preferably of the compound of formula Ia.

The Applicant tested several solvents for the precipitation of the Ca-BOPTA trisodium salt, among which acetone and several short chain alcohols, such as 1-propanol, 2-propanol, 1-butanol and 2-butanol. Nevertheless, these preliminary attempts in isolating Ca-BOPTA trisodium led to unsatisfactory results, such as oily products or solids with unacceptable properties (e.g. gummy, sticky or glassy solids); in some cases, even no precipitation was achieved, i.e. methanol.

The Applicant has thus surprisingly found that it is possible to obtain a suitable solid form of the Ca-BOPTA trisodium salt by adding ethanol to the Ca-BOPTA trisodium salt solution.

In the present description, the expression "suitable solid form" indicates a filterable solid form of the Ca-BOPTA trisodium suitable for pharmaceutical use, having suitable physicochemical properties, such as high solubility, high dissolution rate, high purity and high flowability.

According to a preferred embodiment of the invention, the step c) of the proposed process, comprises adding ethanol to the aqueous solution of Ca-BOPTA trisodium salt to achieve the precipitation of a solid form of the compound of formula Ia.

According to an alternative embodiment of the invention, the step c) of the proposed process can be performed adding the aqueous solution to ethanol.

In an embodiment of the invention, the weight ratio between BOPTA and ethanol is preferably comprised between 1:4 to 1:30 w/w, more preferably from 1:5 to 1:15 w/w, still more preferably from 1:7 and 1:12 w/w.

In a preferred embodiment of this invention, the precipitation of Ca-BOPTA trisodium at step c) is obtained when the concentration of said solution of the calcium complex of formula Ia is comprised between 30% and 80%, preferably between 40% and 75%, still more preferably between 45% and 70%.

For instance, the Applicant observed that with concentrations of the compound of formula Ia lower than 40%, no precipitation occurred, while aqueous solutions with higher concentration than 70% were very viscous and led to the formation of very thin solids difficult to filter and dry.

Step c) is preferably performed at a temperature comprised between 20 and 80° C., more preferably between 40 and 70° C., still more preferably between 50 and 60° C.

According to a still further embodiment of the invention, at the end of the step c) of the proposed process the suspension of the precipitated Ca-BOPTA trisodium salt is cooled to a temperature below 30° C., more preferably below 20° C., still more preferably 10° C.

Step d)

According to the present invention, the step d) of the proposed process comprises collecting the obtained solid form of the calcium complex of formula I, preferably of the calcium complex of formula Ia.

In the present description and claims, the expression "isolation procedure" has its conventional meaning in the chemical field; it indicates any process aimed at separating a substance from a mixture and thus removing substances considered to be impurities.

Examples of suitable isolation procedure are filtration and centrifugation.

In a preferred embodiment of the present invention, the solid form of the Ca-BOPTA trisodium salt of formula Ia is isolated by filtration.

According to an alternative embodiment of the present invention, after the isolation, the Ca-BOPTA trisodium salt is washed with ethanol and dried under reduced pressure, preferably between 0 and $2.0 \times 10^4$ Pa, more preferably between $2.5 \times 10^3$ and $1.5 \times 10^4$ Pa, still more preferably between $5.0 \times 10^3$ and $1.0 \times 10^4$ Pa, and at a temperature at least above 30° C., preferably comprised between 30° C. and 100° C., more preferably between 50° C. a 70° C., still more preferably between 50° C. and 60° C.

Ca-BOPTA trisodium salt prepared in this manner is characterized by a very high quality. The solid form of said salt is colourless and soluble in water and has a purity of 97.0% or more, in some batches of 99.5% or more.

The TG-IR, DSC, IR and elementary analyses were consistent with the proposed compound of formula Ia.

The whole process is characterised by a high reproducibility and workability. As described in detail in the example, the total yield reach about the 94%.

Another aspect of the invention relates to a pharmaceutical composition comprising an effective amount of the compound of formula I, preferably the compound of formula Ia, and one or more pharmaceutically acceptable carriers, galenic diluents and excipients, finding advantageous use as scavenger, for limiting or preventing retention of heavy metals in organs or tissues of living organism.

Said pharmaceutical composition can be prepared according to methods known in the literature, wherein the calcium complex salts of the present invention are dissolved in an aqueous medium, with additives commonly used in a galenic formulation and then the solution is optionally sterilized. Suitable additives are, for example, physiologically buffers, electrolytes, and antioxidants.

In a further aspect the invention relates to the use of the compound of formula I, preferably the compound of formula Ia, or a pharmaceutical composition comprising it, as a medicament, for therapeutic or diagnostic use. In an embodiment, the medical use is as a scavenger agent toward heavy metals, e.g. to prevent, clear or reduce any known or possible retention or accumulation thereof in a living organism. Metals that may be treated (i.e. removed or reduced) with the calcium chelates of the invention include divalent and trivalent metal ions that displace calcium from the complex. Suitable examples include lead; transition metals such as chromium, iron, cadmium, manganese, and mercury; and lanthanides and actinides, including paramagnetic metal ions and radionuclides typically used in MRI diagnostic and nuclear medicine, respectively.

Noteworthy, the process of the invention may be conveniently employed even on a large scale, for the preparation of a CaBOPTA (trisodium) salt intended for the use as scavenger agent in the preparation of pharmaceutical compositions for reducing or preventing metal retention.

The following examples may serve to better illustrate the invention.

EXAMPLES

Example 1: Preparation of Ca-BOPTA Trisodium Salt by Direct Precipitation

In a 1.5 L reactor, equipped with mechanical stirrer, calcium hydroxide (68.20 g, assay 99.1% w/w, 0.912 mol) is suspended in 750 mL of water. At 20° C. BOPTA (500.0 g, assay 91.39%, 0.890 mol) is loaded in portions; then 28% NaOH solution (317.8 g) is added dropwise in about 1 h.

The suspension is stirred for 4 h. At the end a clear solution is obtained and the pH is adjusted to 7.47 adding 28% NaOH.

The solution is partially distilled at 50-60° C. and reduced pressure (50-100 mbar, i.e. $5.0 \times 10^3$-$1.0 \times 10^4$ Pa) to reach a product concentration of 64.9% w/w. Then ethanol (3.85 kg) is added in 2.5 h keeping the temperature at 40-50° C.

The obtained suspension is stirred for further 0.5 h at the same temperature, then is cooled to 0° C. in 4 h and kept at this temperature for 11 h. At the end the solid is isolated by filtration, washed with ethanol (750 g, previously cooled to 0° C.) and dried for 36 h at 50° C. under reduced pressure (p<30 mbar, i.e. <$3.0 \times 10^3$ Pa).

575.8 g of Ca-BOPTA trisodium are obtained (yield 94.5%).

Elementary Analysis (Sample Tq):

| Element | | | | | |
|---|---|---|---|---|---|
| C | H | N | O | Ca | Na |
| 39.90 | 4.87 | 6.20 | 27.38 | 6.04 | 8.58 |

Water (KF): 6.83%

Example 2: Preparation of Ca-BOPTA Trisodium by Inverse Precipitation

In a 2 L reactor, equipped with mechanical stirrer, NaOH in pellets (80.28 g, 2.01 mol) and BOPTA (450.0 g, assay 91.6% w/w, 0.803 mol) are dissolved in 1575 mL of water at 25° C. Then $CaCO_3$ (80.36 g, 0.803 mol) is loaded in portions keeping under stirring in about 1 h.

The mixture is kept at 25° C. for 1 h and then heated to 55° C. for further 4 h to remove carbonic anhydride. At the end the pH is adjusted to 7.05 adding 30% NaOH.

The solution is partially distilled at 50-60° C. and reduced pressure (50-100 mbar, i.e. $5.0 \times 10^3$-$1.0 \times 10^4$ Pa) to reach a product concentration of 51.6% w/w.

In a 5 L reactor 4.92 kg of ethanol are loaded and the concentrated solution is added in 2.5 h at 20° C. The obtained suspension is stirred for a further 1 h and then is filtered. The wet solid is dried for 16 h at 40° C. under reduced pressure (p<30 mbar, i.e. <$3.0 \times 10^3$ Pa).

400.3 g of Ca-BOPTA trisodium are obtained (yield 80.7%).

Example 3—Preparation of Ca-BOPTA Trisodium with 2-Propanol

An aqueous solution of Ca-BOPTA trisodium (200 g, concentration 51.8%), prepared as described in Example 2, is partially distilled at 45° C. and reduced pressure (50-100 mbar, i.e. $5.0 \times 10^3$-$1.0 \times 10^4$ Pa) to reach a 63% concentration.

At the same temperature 2-propanol (655.0 g) is added dropwise in 1.5 h. Then the suspension is cooled to room temperature. An oily sticky product is obtained.

Example 4—Preparation of Ca-BOPTA Trisodium with Acetone

In a 1.5 L reactor, equipped with mechanical stirrer, 30% NaOH solution (297.4 g) and water (238.4 g) are loaded. BOPTA (500.0 g, assay 91.63%, 0.890 mol) is loaded in portions at 20° C.

After complete dissolution, calcium hydroxide (66.1 g, 0.89 mol) is added.

The suspension obtained is stirred for 1 h, heated to 55° C. and kept under stirring for further 4 h. At the end the mixture is cooled to 25° C. h and kept at this temperature overnight. Then the pH is adjusted to 7.01 adding 30% NaOH.

A portion of this aqueous solution of Ca-BOPTA trisodium (200 g, concentration 46.0%), is partially distilled at 40° C. and reduced pressure (50-100 mbar, i.e. $5.0 \times 10^3$-$1.0 \times 10^4$ Pa) to reach a 55.1% concentration.

At the same temperature acetone (911.6 g) is added. Then the suspension is maintained overnight at 40° C. An oily sticky product is obtained.

Example 5—Preparation of Ca-BOPTA Trisodium with 1-Propanol

In a 1.5 L reactor, equipped with mechanical stirrer, calcium carbonate (90.93 g, 0.91 mol) is suspended in 212 mL of water. BOPTA (500.0 g, assay 91.48%, 0.89 mol) and 30% NaOH solution (317.8 g) are added in alternate portions in about 8 h, at 25° C.

The suspension is heated to 50° C. in 1 h, kept under stirring for 3 h. Then the suspension is cooled to 25° C. in 1 h and maintained at this temperature overnight. At the end a clear solution is obtained and the pH is adjusted to 7.0 adding 30% NaOH.

A portion of this aqueous solution of Ca-BOPTA trisodium (110 g, concentration 46.7%) is heated at 40° C. At the same temperature 1-propanol (179.5 g) is added. Then the turbid mixture obtained is heated to 50° C., obtaining complete solution, and cooled to 5° C. in 4 h. An oily product is obtained.

Example 6—Preparation of Ca-BOPTA Trisodium with a Solution at pH 6.1

In a 1 L reactor, equipped with mechanical stirrer, calcium hydroxide (20.26 g, assay 99.1% w/w, 271 mmol) is suspended in 150 mL of water. At 20° C. BOPTA (150.0 g, assay 91.8%, 268 mmol) is loaded in portions; then 30% NaOH solution (89.37 g) is added dropwise in about 1 h.

The suspension is stirred for 16 h. At the end a clear solution with pH 6.07 is obtained.

The solution is partially distilled at 50-60° C. and reduced pressure (50-100 mbar, i.e. $5.0 \times 10^3$-$1.0 \times 10^4$ Pa) to reach a product concentration of 59.03% w/w. Then ethanol (1.06 kg) is added in 2.5 h keeping the temperature at 40° C.

A sticky lump of product is obtained.

Example 7—Preparation of Ca-BOPTA Trisodium with a 10% Mol/Mol Excess of $Ca^{2+}$ In a 1.5 L reactor, equipped with mechanical stirrer, calcium hydroxide (17.64 g, assay 99.1% w/w, 236 mmol) is suspended in 135 mL of water. At 20° C. BOPTA (120.0 g, assay 91.8%, 215 mmol) is loaded in portions; then 30% NaOH solution (71.50 g) is added dropwise in about 1 h.

The suspension is stirred for 16 h. At the end a clear solution is obtained and the pH is adjusted to 7.06 adding 30% NaOH.

The solution is partially distilled at 50° C. and reduced pressure (50-100 mbar, i.e. $5.0 \times 10^3$-$1.0 \times 10^4$ Pa) to reach a product concentration of 65.6% w/w. Then ethanol (993 g) is added in about 2 h keeping the temperature at 40-50° C.

The obtained suspension is stirred for further 0.5 h at the same temperature, then is cooled to 0° C. in 4 h and kept at this temperature for 16 h.

The obtained solid is sticky, forming big lumps and crusts on the reactor wall and cannot be recovered quantitatively.

Example 8—Preparation of Ca-BOPTA Trimeglumine

In a 4 L reactor, equipped with mechanical stirrer, meglumine (174.2 g, 892 mmol) is dissolved in 500 mL of water; at 15-20° C. BOPTA (250.0 g, assay 91.6%, 446 mmol) and calcium hydroxide (34.22 g, assay 99.1% w/w, 457 mmol) are loaded in portions. The mixture is stirred for 16 h at 20° C. At the end a clear solution is obtained and the pH is adjusted to 7.50 adding meglumine.

The solution is partially distilled at 50° C. and reduced pressure (50-100 mbar, i.e. $5.0 \times 10^3$-$1.0 \times 10^4$ Pa) to reach a product concentration of 65.87% w/w.

Then ethanol (2.50 kg) is added in about 2 h keeping the temperature at 40-50° C.

The obtained suspension is stirred for further 0.5 h at the same temperature, then is cooled to 3° C. in 4 h and kept at this temperature for 14 h.

The obtained solid is sticky and forms big lumps.

The invention claimed is:

1. A compound of formula I:

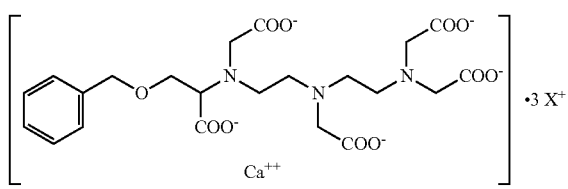

Where $X^+$ represents a monovalent cation selected from an alkali metal cation and ammonium ($NH_4^+$).

2. The compound of claim 1, wherein X is sodium.

3. A process for the preparation of a solid form of the compound claim 1, which comprises:
   a) obtaining an aqueous solution of the compound of formula I by admixing a compound comprising calcium ion, the ligand BOPTA of formula III'

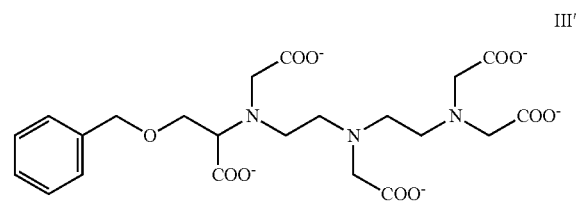

and a compound comprising the cation X in an aqueous solvent;
   b) adjusting the pH of the solution obtained at step a) at a value of from 6.5 to 9.5;
   c) adding ethanol to the obtained solution, to achieve the precipitation of a solid form of compound of formula I;
   d) collecting the obtained solid form of the calcium complex of formula I.

4. The process according to claim 3, wherein the compound comprising calcium ion is calcium hydroxide or calcium carbonate.

5. The process according to claim 3, wherein the compound comprising the cation X of step a) is a base selected from hydroxides or carbonates of alkali metals or of ammonium.

6. The process according to claim 5, wherein the compound comprising the cation X of step a) is sodium hydroxide.

7. The process according to claim 3, wherein at step a) the molar ratio between the compound of formula III' and the compound comprising the cation X is from 1:1.5 to 1:3 mol/mol.

8. The process according to claim 7 wherein said ratio is from 1:2.5 to 1:3 mol/mol.

9. The process according to claim 3, wherein at the end of step a), the aqueous solution contains an excess of free $Ca^{2+}$ with respect to Ca-BOPTA.

10. The process of claim 9, wherein said excess of free $Ca^{2+}$ is lower than 0.09 molar equivalents with respect to Ca-BOPTA.

11. The process of claim 9, wherein said excess of free $Ca^{2+}$ is lower than 0.05 molar equivalents with respect to Ca-BOPTA.

12. The process according to claim 3, wherein step b) comprises adjusting the pH of the aqueous solution of the compound of formula I obtained at step a) by the addition of a base.

13. The process according to claim 12 wherein said base is selected from hydroxides or carbonates of alkali metals or of ammonium.

14. The process according to claim 13, wherein the base is sodium hydroxide.

15. The process according to claim 3 wherein said pH is adjusted at a value of from 7.0 to 8.5.

16. The process according to claim 3, wherein the ratio between the compound of formula III' and ethanol is from 1:4 to 1:30 (w/w).

17. The process according to claim 16, wherein said ratio is from 1:5 to 1:15.

18. A pharmaceutical composition comprising an effective amount of the compound of claim 1, and one or more pharmaceutically acceptable carriers, galenic diluents and excipients.

19. A pharmaceutical composition comprising an effective amount of the compound of claim 2, and one or more pharmaceutically acceptable carriers, galenic diluents and excipients.

* * * * *